United States Patent
Holdaway et al.

(10) Patent No.: US 6,582,368 B2
(45) Date of Patent: Jun. 24, 2003

(54) MEDICAL INSTRUMENT SHEATH COMPRISING A FLEXIBLE ULTRASOUND TRANSDUCER

(75) Inventors: Charles R. Holdaway, San Diego, CA (US); Paul F. Zupkas, 1668 Los Altos Rd., San Diego, CA (US) 92109; David G. Matsuura, Escondido, CA (US)

(73) Assignees: Paul F. Zupkas, San Diego, CA (US); C. Lowell Parsons, San Diego, CA (US)

( * ) Notice: Subject to any disclaimer, the term of this patent is extended or adjusted under 35 U.S.C. 154(b) by 0 days.

(21) Appl. No.: 09/836,880

(22) Filed: Apr. 17, 2001

(65) Prior Publication Data

US 2001/0047134 A1 Nov. 29, 2001

Related U.S. Application Data

(62) Division of application No. 09/164,603, filed on Oct. 1, 1998, now Pat. No. 6,217,518.

(51) Int. Cl.[7] .............................. A61B 8/00; A61B 8/12
(52) U.S. Cl. ..................................... 600/443; 600/462
(58) Field of Search ................................ 600/437, 439, 600/443, 459–471

(56) References Cited

U.S. PATENT DOCUMENTS

| | | | |
|---|---|---|---|
| 3,556,079 A | 1/1971 | Omizo | 128/2 |
| 3,911,924 A | 10/1975 | Zimmer | 128/303.1 |
| 3,933,156 A | 1/1976 | Riggi | 128/303.1 |
| 3,942,530 A | 3/1976 | Northeved | 128/303.15 |
| 3,948,269 A | 4/1976 | Zimmer | 128/303.1 |
| 3,971,383 A | 7/1976 | van Gerven | 128/303.1 |
| 4,018,227 A | 4/1977 | Wallach | 128/303.1 |
| 4,022,215 A | 5/1977 | Benson | 128/303.1 |
| 4,029,102 A | 6/1977 | Barger | 128/303.1 |
| 4,063,560 A | 12/1977 | Thomas et al. | 128/303.1 |
| 4,082,096 A | 4/1978 | Benson | 128/303.1 |
| 4,146,030 A | 3/1979 | Holroyd | 128/303.1 |
| 4,206,609 A | 6/1980 | Durenee | 62/6 |
| 4,206,760 A | 6/1980 | Davis | 128/303.1 |
| 4,207,897 A | 6/1980 | Lloyd et al. | 128/303.1 |
| 4,211,231 A | 7/1980 | Rzasa | 128/303.1 |

(List continued on next page.)

FOREIGN PATENT DOCUMENTS

| | | | |
|---|---|---|---|
| EP | 0 329 492 A2 | 8/1989 | |
| EP | 0 446 645 A1 | 9/1991 | A61B/8/12 |
| EP | 0873 722 A1 | 10/1998 | |
| WO | WO 96/05768 | 2/1996 | |
| WO | WO 97/01988 | 1/1997 | |
| WO | WO 97/29699 | 8/1997 | |
| WO | WO 98/30144 | 7/1998 | |

OTHER PUBLICATIONS

Amertek Medical, Inc. (1998) Sure–Point stepping & stabilizing system for seed implantation http://www.amertek-med.com/image2.htm 6 pgs.

Kapton (1998) High performance films. http://www.kapton.com/indes.htm 6 pgs.

(List continued on next page.)

*Primary Examiner*—Francis J. Jaworski
(74) *Attorney, Agent, or Firm*—Knobbe Martens Olson & Bear LLP (57) ABSTRACT

An ultrasound transducer comprises a sheath body constructed from a nonconductive material. The sheath body is configured to be installed over a medical device. A piezoelectric copolymer transducer is held snugly against the medical device by the sheath body when the ultrasound transducer is installed over the medical device. The piezoelectric copolymer transducer transduces incident ultrasound signals into corresponding electric signals. A ground conductor is coupled to a first surface of the piezoelectric copolymer transducer. A signal conductor is coupled to a second surface of the piezoelectric copolymer transducer and conducts the corresponding electric signals to a proximal end of the medical device.

22 Claims, 6 Drawing Sheets

U.S. PATENT DOCUMENTS

| | | | |
|---|---|---|---|
| 4,236,518 A | 12/1980 | Floyd | 128/303.1 |
| 4,249,536 A | 2/1981 | Vega | 128/349 |
| 4,249,539 A | 2/1981 | Vilkomerson et al. | 128/660 |
| 4,280,499 A | 7/1981 | Sguazzi | 128/303.1 |
| 4,345,598 A | 8/1982 | Zobac et al. | 128/303.1 |
| 4,377,168 A | 3/1983 | Rzasa et al. | 128/303.1 |
| 4,407,294 A | 10/1983 | Vilkomerson | 128/660 |
| 4,412,248 A | 10/1983 | Carmen | 358/112 |
| 4,416,281 A | 11/1983 | Cooper et al. | 128/400 |
| 4,431,006 A | 2/1984 | Trimmer et al. | 128/660 |
| 4,651,310 A | 3/1987 | Kaneki | 367/140 |
| 4,697,595 A | 10/1987 | Breyer et al. | 128/660 |
| 4,698,595 A | 10/1987 | Röschmann | 324/313 |
| 4,706,681 A | 11/1987 | Breyer et al. | 128/642 |
| 4,869,259 A | 9/1989 | Elkins | 128/660 |
| 4,917,097 A | 4/1990 | Proudian et al. | 600/462 |
| 4,946,460 A | 8/1990 | Merry et al. | 606/24 |
| 5,010,886 A | 4/1991 | Passafaro et al. | 128/660.03 |
| 5,042,486 A | 8/1991 | Pfeiler et al. | 128/653 R |
| 5,078,713 A | 1/1992 | Varney | 606/23 |
| 5,084,044 A | 1/1992 | Quint | 606/27 |
| 5,108,390 A | 4/1992 | Potocky et al. | 606/21 |
| 5,109,861 A * | 5/1992 | Walinsky et al. | 600/463 |
| 5,135,001 A * | 8/1992 | Sinofsky et al. | 600/463 |
| 5,139,496 A | 8/1992 | Hed | |
| 5,147,355 A | 9/1992 | Friedman et al. | 606/23 |
| 5,161,536 A | 11/1992 | Vilkomerson et al. | 128/660.07 |
| 5,174,296 A | 12/1992 | Watanabe et al. | 128/662.06 |
| 5,178,148 A | 1/1993 | Lacoste et al. | 128/660.03 |
| 5,197,476 A | 3/1993 | Nowacki et al. | 128/660.03 |
| 5,199,419 A | 4/1993 | Remiszewski et al. | 128/20 |
| 5,211,165 A | 5/1993 | Dumoulin et al. | 128/653.1 |
| 5,215,092 A | 6/1993 | Wray | 128/660.09 |
| 5,234,004 A | 8/1993 | Hascoet et al. | 607/116 |
| 5,243,988 A | 9/1993 | Sieben et al. | 128/662.06 |
| 5,247,938 A | 9/1993 | Silverstein et al. | 128/662.03 |
| 5,254,116 A | 10/1993 | Baust et al. | 606/23 |
| 5,259,384 A | 11/1993 | Kaufman et al. | 128/660.01 |
| 5,259,837 A | 11/1993 | Van Wormer | 604/96 |
| 5,275,166 A | 1/1994 | Vaitekunas et al. | 128/660.03 |
| 5,282,472 A | 2/1994 | Companion et al. | 128/662.06 |
| 5,295,484 A | 3/1994 | Marcus et al. | 128/660.03 |
| 5,307,816 A | 5/1994 | Hashimoto et al. | 128/660.03 |
| 5,313,950 A | 5/1994 | Ishikawa et al. | 128/662.06 |
| 5,325,860 A | 7/1994 | Seward et al. | 128/662.06 |
| 5,370,121 A | 12/1994 | Reichenberger et al. | 128/660.02 |
| 5,385,544 A | 1/1995 | Edwards et al. | 604/22 |
| 5,398,690 A | 3/1995 | Batten et al. | 128/662.05 |
| 5,433,717 A | 7/1995 | Rubinsky et al. | 606/20 |
| 5,437,283 A | 8/1995 | Ranalletta et al. | 600/463 |
| 5,472,405 A | 12/1995 | Buchholtz et al. | |
| 5,474,071 A | 12/1995 | Chapelon et al. | 128/660.03 |
| 5,515,853 A * | 5/1996 | Smith et al. | 600/447 |
| 5,531,742 A | 7/1996 | Barken | 606/21 |
| 5,564,423 A | 10/1996 | Mele et al. | 128/660.02 |
| 5,588,432 A | 12/1996 | Crowley | |
| 5,624,382 A | 4/1997 | Oppelt et al. | |
| 5,647,868 A | 7/1997 | Chinn | |
| 5,657,760 A | 8/1997 | Ying et al. | |
| 5,672,172 A | 9/1997 | Zupkas | |
| 5,830,144 A * | 11/1998 | Vesely | 600/459 |
| 6,019,725 A * | 2/2000 | Vesely et al. | 600/447 |
| 6,217,518 B1 * | 4/2001 | Holdaway et al. | 600/443 |

OTHER PUBLICATIONS

Flexible Circuitry information (1998) world wide web 9 pgs.

Vernitron (1984) Modern piezoelectric ceramics. PD 9247 1–8.

Blasko, J.C., et al. (1996) Should brachytherapy be considered a therapeutic option in localized prostate cancer? The urologic clinics of north America 23:633–650.

Boring, C.C. et al. (1993) Cancer Statistics, 1993. CA Cancer Journal for Clinicians 42(1):7–26.

Coleman, D.J., et al. (1986) Therapeutic Ultrasound. Ultrasound in Med. & Biol. 12:633–638.

DeReggi, A.S., et al. (1981) Piezoelectric polymer probe for ultrasonic applications. J. Acoust. Soc. Am. 69:854–859.

Fleming, C. et al. (1993) A Decision Analysis of Alternative Treatment Strategies for Clinically Localized Prostate Cancer. JAMA 269(20):2650–2658.

Gage, A.A. (1992) Cryosurgery in the Treatment of Cancer. Gynecology & Obstetrics 174:73–92.

Hilaris, B.S. (1997) Brachytherapy in cancer of the prostate: An historical perspective. Seminars in Surgical Oncology 13:399–405.

Holm, H.H. (1997) The history of interstitial brachytherapy of prostatic cancer. Seminars in Surgical Oncology 13:431–437.

Hunt, J.W., et al. (1983) Ultrasound transducers for pulse–echo medical imaging. IEEE Transactions on Biomedical Engineering vol. BMI–30, No. 8 453–481.

Klein, E.A. (1992) Prostate Cancer: Current Concepts in Diagnosis and Treatment. Cleveland Clinic Journal of Med. 59(4):383–389.

Littrup, P.J. et al. (1993) The Benefit and Cost of Prostate Cancer Early Detection. CA Cancer Journal for Clinicians 43(3):134–149.

Litwin, M.S. et al. Why Do Sicker Patients Cost More? A Charge–Based Analysis of Patients Undergoing Prostatectomy. Journal of Urology 149:84–88.

Meijer, S. et al. (1992) Cryosurgery for Locally Recurrent Rectal Cancer. European Journal of Surgical Oncology 18:255–257.

Mettlin, C. et al. (1993) Trends in Prostate Cancer Care in the United States, 1974–1990: Observations from the Patient Care Evaluation Studies of the American College of Surgeons Commssion on Cancer. CA Cancer Journal for Clinicians 43(2):83–91.

Nori, D., et al. (1997) Current issues in techniques of prostate brachytherapy. Seminars in Surgical Oncology 13:444–453.

Onik, G. et al. (1988) US Caracteristics of Frozen Prostate. Radiology 168:629–631.

Porter, A.T., et al. (1993) Prostate brachytherapy. Cancer supplement 71:953–958.

Schoenwald, J.S., et al. (1983) PVF2 transducers for acoustic ranging and imaging in air. Ultrasonics symposium 577–580.

Telang, D.J. et al. (1992) Radical Surgery in the Treatment of Localized Carcinoma of the Prostate. Henry Ford Hosp Med J 40(1 & 2):108–110.

Watson, L.R. (1997) Ultrasound anatomy for prostate brachytherapy. Seminars in surgical oncology 13:391–398.

White, J.R., et al. (1997) Brachytherapy and breast cancer. Seminars in surgical oncology 13:190–195.

Whitmore, W.F., Jr. (1993) Management of Clinically Localized Prostatic Cancer, An Unresolved Problem. JAMA 269(20):2676–2677.

* cited by examiner

MEDICAL INSTRUMENT SHEATH COMPRISING A FLEXIBLE ULTRASOUND TRANSDUCER

RELATED APPLICATIONS

This is a divisional application of application Ser. No. 09/164,603, filed Oct. 1, 1998, which issued into U.S. Pat. No. 6,217,518 on Apr. 17, 2001, which is hereby incorporated by reference.

BACKGROUND OF THE INVENTION

I. Field of the Invention

The present invention relates to medical devices. More particularly, the present invention relates to a sheath for use with medical devices.

II. Description of the Related Art

The use of minimally invasive surgical techniques has dramatically affected the methods and outcomes of surgical procedures. Physically cutting through tissue and organs to visually expose surgical sites in conventional "open surgical" procedures causes tremendous blunt trauma and blood loss. Exposure of internal tissues and organs in this manner also dramatically increases the risk of infection. Trauma, blood loss, and infection all combine to extend recovery times, increase the rate of complications, and require a more intensive care and monitoring regiment. The result of such open surgical procedures is more pain and suffering, higher procedural costs, and greater risk of adverse outcome.

In contrast, minimally invasive surgical procedures cause little blunt trauma or blood loss and minimize the risk of infection by maintaining the body's natural barriers to infection. Minimally invasive surgical procedures result in faster recoveries and cause fewer complications than conventional surgical procedures. Minimally invasive procedures, such as laparoscopic, brachytherapy, endoscopic, or cystoscopic surgery, have replaced more invasive surgical procedures in many areas of medicine. Due to technological advancements in areas such as fiber optics, micro-tool fabrication, noninvasive visualization, and material science, more easily operated and more cost effective tools are available to the physicians for use in minimally invasive procedures. However, a host of technical hurdles still exists that limit the efficacy and increase the difficulty of minimally invasive procedures.

One critical aspect of minimally invasive surgical techniques is the ability of the operator to visualize the position of surgical instruments within the body and to determine the extent of the manipulation of organs and tissues caused by the surgical instruments. For example, percutaneous coronary angioplasty (PTCA) uses fluoroscopy to position a tiny balloon at the end of a long flexible catheter in a coronary artery where a stricture has reduced blood flow to the heart. Another example of a minimally invasive procedure is arthroscopic surgery in which fiber optic visualization is used to position and control small tools within bone joints to repair, ablate, or remove tissue.

Fiber optic and fluoroscopic visualization require a vessel, duct, or cavity into which a transparent or radiopaque fluid can be injected. However, procedures not involving a vessel, duct, or cavity where a fluid can be injected and contained require other methods of visualization. For example, the manipulation of soft tissue organs requires entirely different methods of visualization. In such procedures, visualization techniques such as magnetic resonance imaging (MRI) or ultrasound which distinguish the borders and shapes of soft tissue organs or masses are used.

MRI has been particularly effective in providing detailed visualization of damage or growth of soft tissues surrounded by other organs and structures. MRI measures the radio frequency (RF) signals emitted by the nuclei of atoms subjected to a transient magnetic field while in a strong static field. However, the size, cost, complexity, and nature of MRI systems may make them poor candidates for visualization in many surgical procedures.

Ultrasound imaging relies on the reflection of high frequency sound waves at interfaces of varying acoustic impedance to create a two dimensional picture of internal body structures. Many prior art ultrasound imaging systems exhibit undesirable features such as a lack of structural resolution, phantom and ghost images created by scattered sound waves and limited visualization due to obstructions in the field of view. However, ultrasound does provide a lower cost, less complicated and more compact alternative to MRI. Ultrasound imaging systems can typically be operated by one person, are a fraction of the cost and size of an MRI system, are mobile, and are less restrictive on the operating environment.

Modern ultrasound technology has expanded the application of minimally invasive surgical techniques into areas in which direct surgical intervention had previously been the only option. One surgical technique to which modern ultrasound imaging has been applied is cryosurgery. Cryosurgery involves the freezing of diseased tissue. Cryosurgery has been used for decades with limited success to destroy diseased tissue throughout the body. Historically, cryosurgery has been limited in its application to the destruction of tissue on the surface of the body or in a space where the visible manipulation of tissue was possible. Recently the role of cryosurgery has been expanded to include the application of cryosurgery in a minimally invasive manner. Minimally invasive techniques were made possible by advances in the ability to visualize soft tissues by ultrasound imaging. Ultrasound imaging allows the surgeon to visualize tissue or organ "landmarks" within the patient's body and, thereby, correctly position the freezing probe or cryoprobe within the soft tissue.

The surgical procedure for destroying a target tissue with cryosurgery begins by placing the probe in the target tissue mass. Ultrasound imaging is typically used to guide the probe in a minimally invasive manner. An ultrasound transducer on the probe in close proximity to the freezing element is used to facilitate the positioning of the probe. The ultrasound transducer on the probe generates an ultrasound signal in response to detection of an incident ultrasound signal from an imaging system. The response signal is detected by the imaging system causing an image to be displayed on the monitor of the imaging system. The response signal radiates from the ultrasound transducer on the probe, thus, defining the location of the probe tip and freezing element.

Prior art ultrasound transducers use ferroelectric piezoceramic transducer elements. Ferroelectric transducers are made of materials such as lead zirconate titanate (PZT) and, therefore, are glasslike and brittle. Due to their brittle nature, ferroelectric elements are susceptible to breaking or cracking. To avoid breakage during the surgical process, the ferroelectric transducer must be mounted securely to the medical device within a protective enclosure as an integral part of the medical device. These requirements add cost and complexity to the design of the medical device.

The resonant frequency of ferroelectric transducers over which they are useful as ultrasound transducers is determined by the thickness of the device. A typical ferroelectric element has a hallow a cylindrical shape. Electrodes are placed on the inner and outer cylindrical surfaces of the transducer. Ferroelectric transducers are narrow band devices, meaning the frequency bandwidth over which a ferroelectric element is useful as a transducer is limited. For example, a ferroelectric element with a cylindrical wall thickness of approximately 0.015 inches is useful as an ultrasound transducer over a range from about 5 Megahertz (MHz) to about 10 MHz. Practical manufacturability concerns constrain the minimum size of ferroelectric elements in cylindrical shapes to a cylindrical wall thickness of approximately 0.012 inches meaning that the actual diameter of the devices is significantly larger. Inclusion of an element with such a relatively large size can adversely impact the design of the medical device and interfere with the efficient operation of the device.

A variety of different medical devices may benefit from the inclusion of an ultrasound transducer. The task of redesigning the large variety of medical instruments to include an ultrasound transducer is quite burdensome, requiring extensive redesign, retesting and manufacturing retooling. Therefore, the inclusion of an ultrasound transducer on a large variety of medical device may be financially prohibitive.

In addition, the presence of an ultrasound transducer is not required for all procedures which might be carried out by a particular medical device. Therefore, inclusion of an unnecessary ultrasound transducer can add cost and complication to a medical device as well as sub-optimal design constraints. Therefore, there are many situations in which it is advantageous to use medical devices which do not contain an ultrasound transducer.

Therefore, it is apparent that there has been a long felt need in the industry to have an efficient means and method of providing ultrasound capabilities to a variety of medical instruments as needed without significantly interfering with the performance of the device. The present invention provides an elegant means and method for satisfying this need.

SUMMARY OF THE INVENTION

An ultrasound transducer comprises a sheath body constructed from a nonconductive material, the sheath body is configured to be installed snugly over a medical device. A piezoelectric copolymer transducer is held snugly to the medical device by the sheath body when the ultrasound transducer is installed over the medical device. The piezoelectric copolymer transducer transduces incident ultrasound signals into corresponding electric signals. A ground conductor is coupled to a first surface of the piezoelectric copolymer transducer. And a signal conductor is coupled to a second surface of the piezoelectric copolymer transducer and conducts the corresponding electric signals to a proximal end of the medical device.

In one embodiment, the medical device comprises a manipulator for manipulating tissue within a zone of manipulation and the piezoelectric copolymer transducer is disposed within the zone of manipulation and responds to receipt of an incident radiated signal by generation of a responsive radiated signal while the manipulator manipulates the tissue within the zone of manipulation. The ultrasound transducer may comprise electronics coupled to the piezoelectric copolymer transducer which receive a timing input from a scanner so that when a signal level of the incident radiated signal falls below a level at which the ultrasound transducer may detect the incident signal, the piezoelectric copolymer transducer generates a timed radiated signal based upon the timing signal.

In another embodiment, the piezoelectric copolymer transducer is further for transducing input electric signals conducted by the signal conductor into ultrasound signals radiated by the piezoelectric copolymer transducer. A scanner may produce the incident ultrasound signals, detect the ultrasound signals radiated by the piezoelectric copolymer transducer and produce a corresponding image.

In one embodiment, the piezoelectric copolymer transducer is deposited on the sheath body. In another embodiment, the signal conductor is deposited on the sheath body. In yet another embodiment, the ground conductor is disposed on the sheath body to cover the signal conductor when the ultrasound transducer is installed over the medical device, thereby, operating to shield the signal conductor from ingress signals. The ground conductor may be wider than the signal conductor. The ground conductor is directly coupled to the medical device in order to provide a common ground potential.

In one embodiment, the piezoelectric copolymer transducer is disposed on the sheath body so as to be located at a tip of the medical device when the ultrasound transducer is installed thereon. The sheath body may comprise openings in order to facilitate performance of an intended purpose of the medical device.

The ultrasound transducer may further comprise a signal recovery and production unit for producing a input electric signal on the signal conductor responsive to the incident ultrasound signal detected by the piezoelectric copolymer transducer. In another embodiment, the medical device manipulates tissue and a means for analyzing is coupled to the signal conductor. The means for analyzing accumulates a set of values of the corresponding electric signals over time in order to determine a predicted measure of manipulation induced by the medical device. In yet another embodiment, the means for analyzing comprises an imaging system for displaying an image derived from signals generated by a scanner and an image of the predicted measure of manipulation. In one embodiment, the ultrasound transducer comprises a second piezoelectric copolymer transducer.

In yet another embodiment, the ultrasound transducer comprises a transformer coupled to the signal conductor which transforms an electrical impedance of the piezoelectric copolymer transducer to a lower value. The transformer may be a toroid. The transformer may be integrated into an electrical connector which couples the signal conductor to a signal recovery and production unit.

In one embodiment, the piezoelectric copolymer transducer is constructed from polyvinylidene difluoride (PVDF). In another embodiment, the piezoelectric copolymer transducer is constructed from polyvinyl difluoride (PVF). In yet another embodiment, the piezoelectric copolymer transducer is constructed from copolymers of vinylidene fluride. In yet another embodiment, the piezoelectric copolymer transducer is deposited on the sheath body so as to form a cylindrical band around the ultrasound transducer. The cylindrical band may be about 1 to 10 millimeters in width. The cylindrical band may be about 25–150 micrometers thick. The piezoelectric copolymer transducer may exhibit a relatively flat response to the incident ultrasound signals in the range of 1 to 10 Megahertz.

In one embodiment, the sheath body is constructed from of a material that shrinks when exposed to some external effect. In another embodiment, the sheath body is constructed from polytetrafluoroethylene. In yet another embodiment, the sheath body is constructed from a polymer. In yet another embodiment, the sheath body is constructed from mylar.

The sheath body may be constructed to be about 10% smaller than an outside diameter of the medical device. The sheath body is constructed from a flat sheet of material having two opposing edges sealed together lengthwise.

The medical device may be a biopsy needle, brachytherapy needle, breast biopsy probe or a cryoprobe. The ultrasound transducer may be intended for a single use. In one embodiment, the ultrasound transducer operates independently from the medical device. The ultrasound transducer may be suitable for use with a variety of different medical devices.

A method of performing a medical procedure comprising ultrasound functionality has the step of installing a disposable sheath comprising a copolymer transducer over a medical device. The disposable sheath is coupled to a signal recovery and production unit. An area of tissue is exposed to an incident ultrasound signal. The medical device is disposed within the area of tissue. A corresponding electric signal is detected from the copolymer transducer at the signal recovery and production unit. In one embodiment, the method comprises the step of responding to receipt of the corresponding electric signal by generation of a responsive electric signal which is transduced by the copolymer transducer to create a responsive ultrasound signal. In another embodiment, the method further comprises the step of responding to receipt of a timing signal from a scanner by generation of the responsive electric signal which is transduced by the copolymer transducer to create the responsive ultrasound signal when a level of the incident ultrasound signal falls below a detectable level.

The medical device may be a biopsy needle, a brachytherapy needle, a breast biopsy probe or a cryoprobe. The disposable sheath may be intended for a single use. The disposable sheath may comprise a sheath body constructed polytetrafluoroethylene, a polymer or from from mylar. In one embodiment, the disposable sheath comprises a stretchable sheath body constructed to be smaller than an outside diameter of the medical device. In another embodiment, the disposable sheath comprises a sheath body constructed from of a material that shrinks when exposed to some external effect. The disposable sheath may comprise a sheath body comprising openings in order to facilitate performance of an intended purpose of the medical device. In one embodiment, the signal recovery and production unit accumulates a set of values of the corresponding electric signal over time in order to determine a predicted measure of manipulation induced by the medical device.

In one embodiment, the disposable sheath further comprises a second piezoelectric copolymer transducer. The copolymer transducer may be constructed from polyvinylidene difluoride (PVDF), polyvinyl difluoride (PVF) or copolymers of vinylidene flurride.

In one embodiment, the method comprises the step of generating an input electric signal at the signal recovery and production unit wherein the input electric signal is transduced into an ultrasound signal radiated by the copolymer transducer. In another embodiment, the method comprises the step of activating the medical device to manipulate tissue. In yet another embodiment, the method further comprises the steps of withdrawing the medical device from the patient, removing the disposable sheath from the medical device and disposing of the disposable sheath.

BRIEF DESCRIPTION OF THE DRAWINGS

The features and advantages of the present invention will become more apparent from the detailed description set forth below when taken in conjunction with the drawings in which like reference characters correspond throughout and wherein.

DETAILED DESCRIPTION OF THE PREFERRED EMBODIMENT

The present invention comprises a disposable sheath and a flexible ultrasound transducer. The sheath is adapted to be inserted over a medical device for temporary use in conjunction with the device. In this way, the sheath can be used to provide ultrasound functionality to an existing medical device without modification of the device. After use, the sheath may be disposed of with the device or removed from the device and disposed of. The sheath is designed to operate in conjunction with the profile of a medical device, thereby, reducing any interference of the sheath with the function of the medical device.

In order to be mounted on a sheath, the ultrasound transducer must be flexible to allow for expansion or contraction of the sheath assembly to create a snug fit over the medical device. Ferroelectric ultrasound transducers, such as those incorporated into prior art ultrasound medical devices, are neither thin nor flexible and, therefore, are not suited for incorporation into a flexible sheath. If one attempted to integrate a ferroelectric ultrasound transducer into a flexible sheath design, the ferroelectric ultrasound transducer would likely break when the sheath was stretched or shrunk to fit snuggly over the medical device.

The present invention incorporates a copolymer material with piezoelectric properties such as polyvinylidene difluoride (PVDF), polyvinyl difluoride (PVF), or copolymers of vinylidene fluoride to act as an ultrasound transducer. In order to function properly, the copolymer transducer must be held firmly against a rigid structure in a snug configuration. The sheath design can accommodate this need by holding the copolymer transducer snug against the medical device. In addition, a snug fit between the sheath and the medical device can act as a means of attachment of the sheath to the medical device. The snug fit also can serve to minimize the interference of the sheath with the intended purpose of the medical device.

When subjected to electric signals, the ultrasound transducer material actually moves as its thickness grows and shrinks. A snug fit between the sheath a the medical device provides the ultrasound transducer a rigid backing. When held firmly against a rigid backing, the ultrasound transducer is constrained to deflect in an outward radial direction. and, therefore, to direct the ultrasound signals out in a radial direction.

Typically, the sheath is formed into a cylindrical or other shape that fits onto a variety of medical devices of varying shapes and sizes. In one embodiment, the sheath body is formed from nonconductive elastic materials that stretch when placed in tension such as polymers, plastics, rubbers, mylars, or some other suitable elastic material. In such a case, the sheath is designed to be slightly smaller than the medical device with which it is used. For example, the finished sheath may be about 10% smaller than the medical device on which it is installed. As the sheath stretches to cover the medical device, a snug fit between the sheath and the medical device is created.

Alternatively, the sheath body may be constructed of a material that shrinks when exposed to some external effect. For example, the sheath body may be constructed of shrink tube such as polytetrafluoroethylene (PTFE) which shrinks when exposed to heat. In such a case, the sheath body is made larger than the medical device with which it is used. Once the sheath has been positioned on the medical device, the sheath is exposed to heat to form a snug fit with the device.

After use, the sheath may be removed from the medical device and discarded. The medical device may then be reused—either in conjunction with another sheath or alone. The sheath may also be used in conjunction with a disposable medical device, where both the sheath and device are disposed of at the end of the procedure.

A system of electrical circuitry is used to receive, interpret, and transmit electrical signals generated by the copolymer transducer on the sheath. The system may be external, internal, or a combination of both external and internal to the sheath. For example, in one embodiment, external electrical circuitry comprises a signal recovery and production unit. The signal recovery and production unit receives the output electric signal generated by the copolymer transducer when exposed to ultrasound energy pulses. The signal recovery and production unit analyzes the output electric signal from the copolymer transducer and produces a corresponding response input electric signal to the copolymer transducer such as in accordance with U.S. Pat. No. 5,672,172. The copolymer transducer coverts the input electric signal to an ultrasound signal which may be detected by an ultrasound scanner. The signal recovery and production unit may also be used to analyze the output electric signal in order to determined an extent of tissue manipulation such as in accordance with co-pending U.S. patent application Ser. No. 08/982,753.

Copolymer materials with ultrasound transducing properties are commercially available from a number of vendors. These devices are often marketed as pressure or motion sensors. For example, copolymer materials may be used to sense the presence of road traffic in order to trigger traffic indications. AMP Incorporated, Piezo Film Sensor Division, of Valley Forge, Pa., USA markets a number of copolymer transducers such as the 28 $\mu$m (AMP part #1-1003703-4),52 $\mu$m (AMP part #2-1003703-4), or 110 $\mu$m (AMP part #3-1003702-4) metalized piezo film sheets. In one embodiment, the copolymer transducer outputs approximately 1 mW of acoustic power when driven by a 10 V peat-to-peak square wave over a frequency range of 2 to 9 MHz.

Ultrasound transducers made from copolymer materials have a number of desirable characteristics in contrast to other piezoelectric transducer materials such as quartz or ceramic devices. For example, the copolymer materials can be deposited on a surface in varying thickness which allows the characteristics of the resulting ultrasound transducer to also vary. Preprinted, commercially available copolymer transducers range in thickness from 28 to 110 micrometers ($\mu$m) and are available from a number of companies.

Ultrasound transducers made from copolymer materials act as transducers over a relatively wide bandwidth. For example, ultrasound transducers made from copolymer materials can be designed to have a nearly flat response to ultrasound over the range of 1–10 MHz. Typically, ceramic and quartz transducers operate over a much more narrow bandwidth. Broadband performance is advantageous because the transducer can operate to detect a wide range of signals and, therefore, is compatible for use in conjunction with a large range of devices.

Copolymer transducers also have a high acoustical transparency in liquid media.

This transparency is created by the similarity in the acoustic impedance between copolymer transducers and liquid media and the small thickness of the transducers in relation to the wavelengths involved. For example, water has an acoustic impedance of $1.48 \times 10^6$ kg/sec-m$^2$ compared to the acoustic impedance of a copolymer transducer at $2.5 \times 10^6$ kg/sec-m$^2$, ceramic at $30 \times 10^6$ kg/sec-m$^2$, and quartz piezoelectric at $14.3 \times 10^6$ kg/sec-m$^2$. The similarity of acoustic impedance between copolymer transducers and liquid media, such as water, blood, or tissue, means a smaller portion of the energy from an incident wave from an ultrasound source is reflected by the interface between the copolymer transducer and the liquid media. In contrast, a significant portion of incident acoustic energy is reflected by the interface between ceramic or quartz piezoelectric transducers and a liquid media, thus, decreasing the energy of the signal passing into the liquid media.

A copolymer transducer is also more compliant than ceramic or quartz piezoelectric transducers. For example, a copolymer transducer has a stiffness of 2 Newton per meter squared (N/m$^2$) compared to approximately 80 N/m$^2$ for ceramic or quartz piezoelectric transducers. The compliant nature of the copolymer transducer is crucial to the ability of the ultrasound transducer to be integrated with a flexible sheath. In addition, copolymer transducers are considerably less expensive to manufacture than quartz or ceramic transducers making them much more suitable for disposable applications.

The electrical impedance of copolymer transducers can be extremely high. The impedance of a copolymer transducer increases as the thickness and surface area of the transducer increase. A typical copolymer transducer used in association with the invention has an electrical impedance of about 1–5 Megohms (M$\Omega$).

Figure 1:
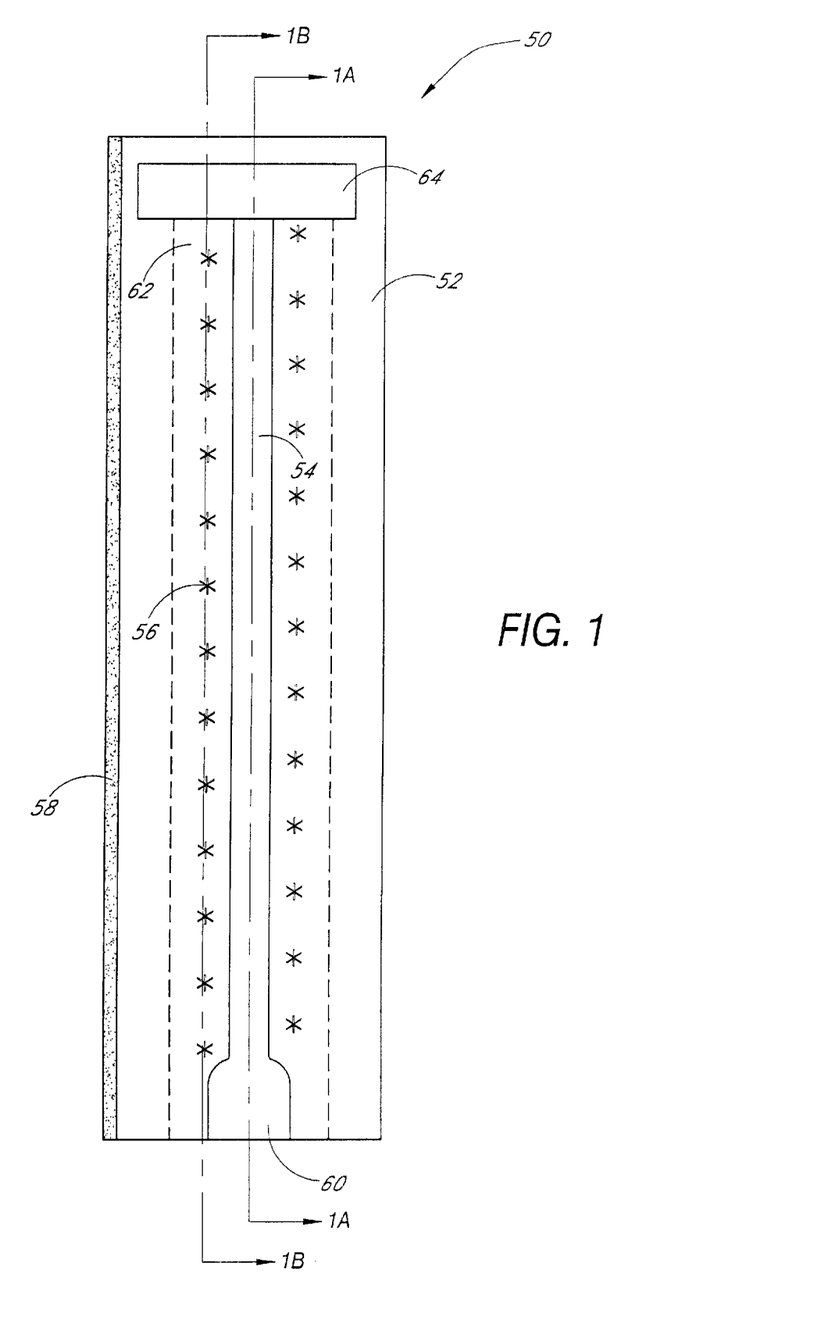
FIG. 1 is a perspective view showing a partially assembled sheath.

FIG. 1 is a perspective view showing a partially assembled sheath 50. As seen in FIG. 1, the partially assembled sheath 50 is a flat sheet of material having two opposing edges which are sealed together lengthwise to create a cylindrical configuration. The sheath 50 is intended to be assembled by attaching an adhesive strip 58 to the opposing edge of the sheath body 52. The adhesive may be epoxy or other bonding agent. Alternatively, the opposing edges may adhere to one another by melting together. In addition to adhesives, any number of mechanisms can be used to form a cylindrical shape. For example, the sheath may be constructed from a continuous condom like structure which assumes a cylindrical shape without the use of adhesives.

In the configuration shown in FIG. 1, a copolymer transducer 64 is deposited or otherwise attached to the sheath body 52. The copolymer transducer 64 may be large enough to form a cylindrical band around the sheath 50 when the sheath 50 is assembled. In one embodiment, the copolymer transducer 64 may be approximately 1 to 10 millimeters in width and 25 to 150 micrometers thick. The copolymer transducer 64 is bonded to a signal conductor 54 using, for example, a conductive epoxy, creating an electrical connection between the inner surface of the copolymer transducer 64 and the signal conductor 54. When assembled, the signal conductor 54 is on the interior surface of the cylindrical shape sheath. Although other configurations are possible, in the configuration shown in FIG. 1, the copolymer transducer 64 is mounted at the distal end of the sheath body 52 and the signal conductor 54 runs the length of the sheath body 52 to a terminal connector 60 at the proximal end of the sheath body 52. The signal conductor 54 may be coated so as to be electrically isolated from anything coming in direct contact with the sheath 50.

As noted above, the copolymer transducer 64 is both broadband and high impedance. For this reason, the signal conductor 54 is particularly susceptible to noise induced from external electric and magnetic fields. The undesired signals can emanate from other electrical devices in the room such as other medical, mechanical and communication devices. For example, local communication networks such intercoms, cellular telephones, and CB radios may transmit signals or produce spurs within the wide bandwidth supported by the sheath 50.

The embodiment shown in FIG. 1 has been designed to reduce such undesired signal ingress by shielding the signal conductor 54 between a ground conductor 62 and the medical device. The ground conductor 62 is shown as printed or otherwise attached to the outer surface of the sheath body 52 but insulated from the signal conductor 54. In one embodiment, the ground conductor 62 is wider in width than the signal conductor 54 and the ground conductor 62 covers the signal conductor 54 in the assembled configuration. In one embodiment, either or both of the signal conductor 54 and ground conductor 62 may utilize flexible circuit technology employing polyimide film such as KAPTON® marketed by DuPont High Performance Films, Circleville, Ohio. The ground conductor 62, as shown in FIG. 1, is wider than the signal conductor 54, thus, allowing grounding brushes 56, through holes in the sheath body 52, to electrically connect the ground conductor 62 to the luminal surface of the assembled sheath without contacting the signal conductor 54. When the sheath 50 is installed on a medical device, the grounding brushes 56 make electrical contact with the surface of the device. If the device surface is electrically conductive, the grounding brushes 56 ground the device to a common potential with the sheath 50 and connected control devices. In this way, the signal conductor 54 is shielded from external electric and magnetic fields. In alternative embodiment, the ground conductor 62 encircles the assembled sheath.

Figure 1A:
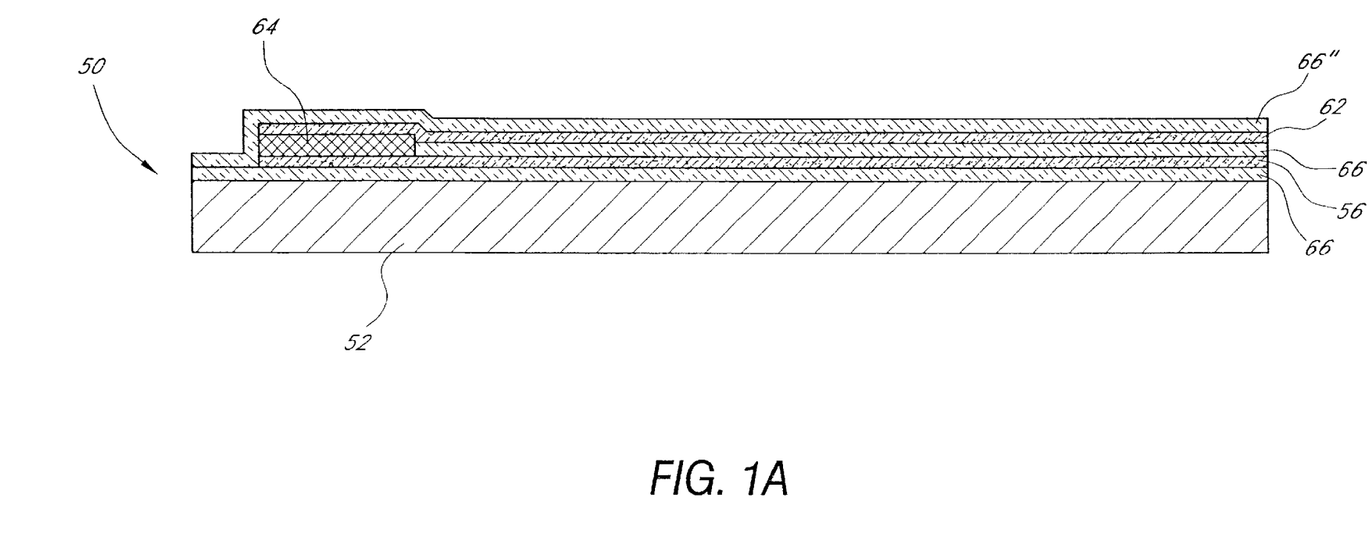
FIG. 1A is a cross sectional view of the sheath 50 taken along the line 1A—1A of FIG. 1.

FIG. 1A is a cross sectional view of the sheath 50 taken along the line 1A—1A as shown in FIG. 1. The sheath body 52 is bonded to an insulating layer 66, such as formed from KAPTON polyimide film. In an alternative embodiment, the sheath body 52 and the insulating layer 66 are fabricated from a common nonconductive material. The signal conductor 54 is deposited over the insulating layer 66 forming the interior electrode of the copolymer transducer 64 and an electrical lead connecting the electrode to the terminal connector 60. The signal conductor 54 is made of an electrically conductive material such as copper, silver, or other suitable material. A second insulating layer 66' is bonded over the lead portion of the signal connector 54. The copolymer transducer 64 is deposited on the electrode portion of the signal conductor 54. The ground conductor 62 is deposited over the insulating layer 66' and copolymer transducer 64, forming the exterior electrode of the transducer and an electrical lead connecting the electrode to the terminal connector 60. In one embodiment, the ground conductor 62 is made of similar materials as the signal conductor 54. A final insulating layer 66" is bonded to the ground conductor 62.

Figure 1B:
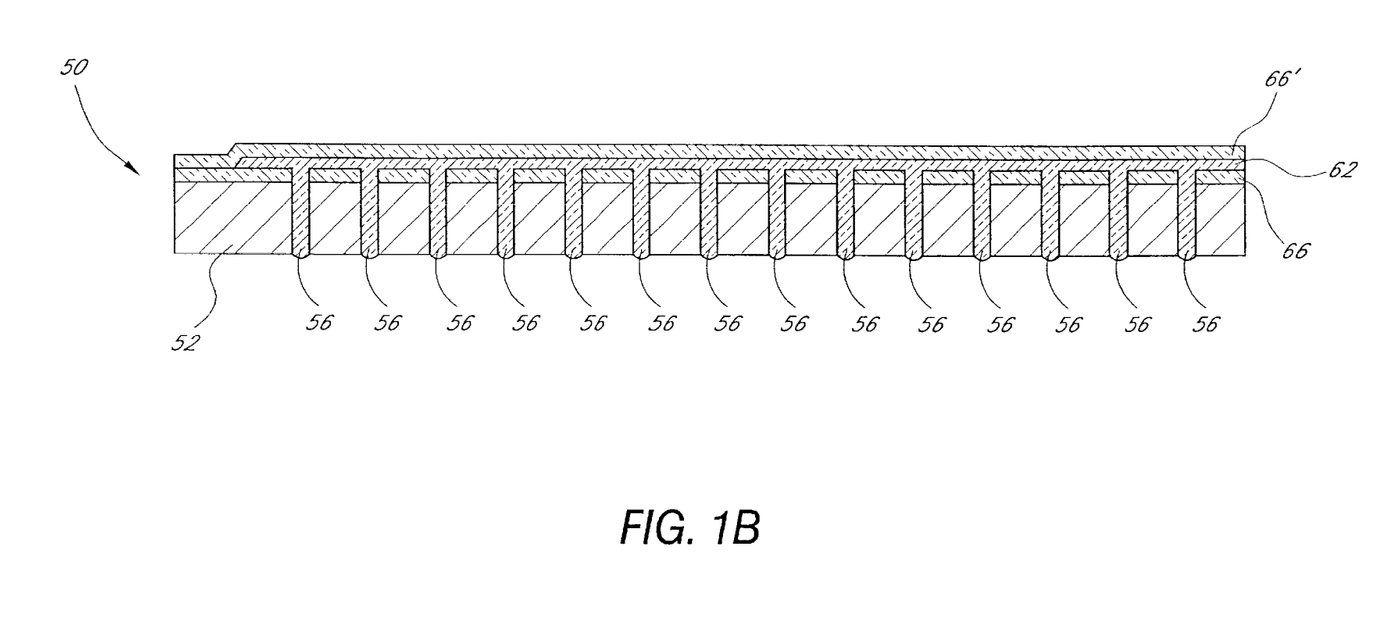
FIG. 1B is a cross section view of the sheath assembly 50 taken along the line 1B—1B of FIG. 1.

FIG. 1B is a cross section view of the sheath assembly 50 taken along the line 1B—1B of FIG. 1. FIG. 1B shows the grounding brushes 56 passing through the sheath body 52. The ground conductor 62 is deposited on the insulating layer 66' in a manner which extends beyond the borders of the lead portion of the signal conductor 54, thus, allowing the grounding brushes 56 to pass through to the interior surface of the sheath body 52 through openings in the sheath body 52 and other intervening layers. The exposed surface of the grounding brushes 56 connects the ground conductor 62 to the surface of the device when the sheath body 52 is installed on a device.

The actual diameter of the assembled sheath 50 can vary in proportion to the medical device with which it is used. The size should be appropriate to assure a snug fit between the transducer and the rigid medical device to which it is attached in order to assure the proper operation of the transducer.

The sheath may be designed to facilitate the continued performance of the medical device for its intended purpose. For example, a sheath for use with a suction device may be designed with an opening at the distal end. A sheath for use with a cryosurgical device may have openings within the sheath body in order to facilitate the conduction of heat energy between the medical device and the tissue it is treating. In addition, an opening at the distal end of the sheath may facilitate creating a snug fit between the sheath and the medical device. A distal opening allows the sheath to be installed at any position along the length of the device that creates a snug fit between the device and the sheath.

A single sheath may comprise more than one copolymer transducer. The second copolymer transducer may be useful for more precise replacement of the medical device if it should shift during a procedure. The second copolymer transducer may also be used to detect a level of manipulation at a second point or to detect a relative level of manipulation at a second point. Additional information concerning the use and usefulness of a second transducer can be found in the above mentioned U.S. patent application Ser. No. 08/982, 753.

Figure 2:
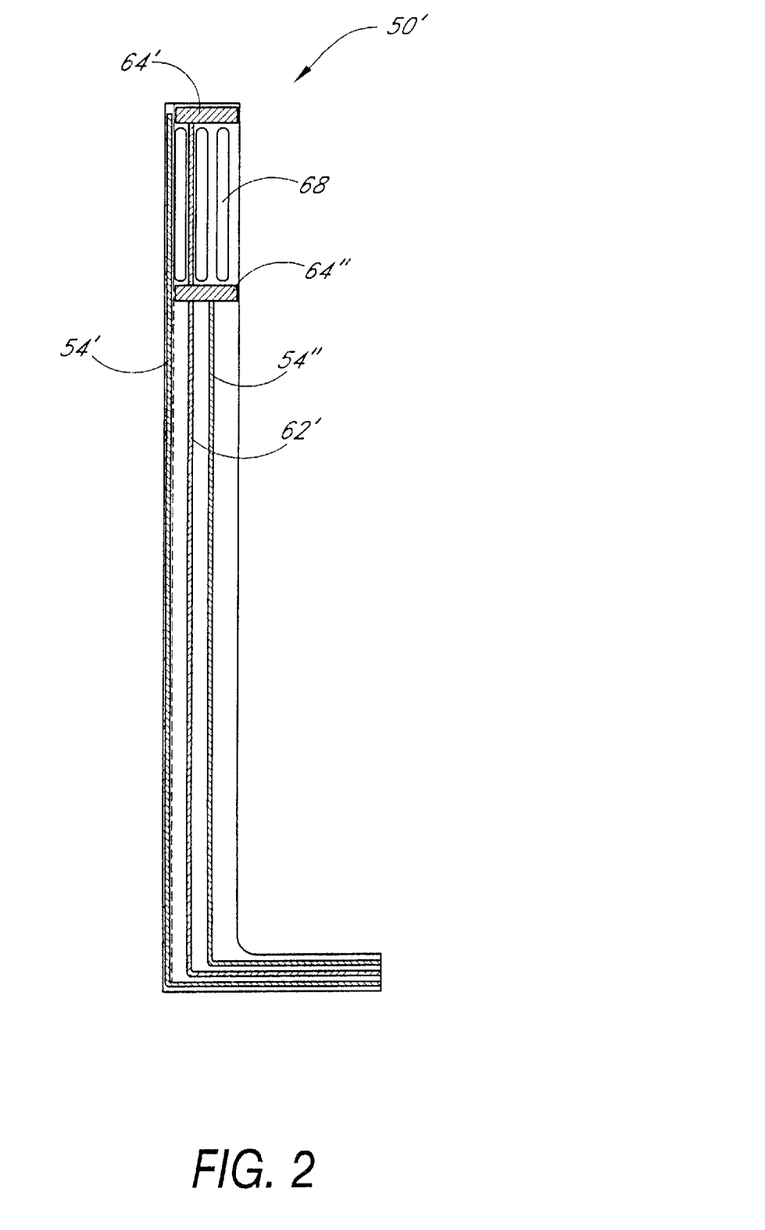
FIG. 2 is a perspective view showing an alternative embodiment a partially assembled sheath.

FIG. 2 is a perspective view of an embodiment of a partially assembled sheath 50' for use in cryosurgical procedures. The sheath 50' comprises a first and a second copolymer transducers 64' and 64". The signal conductor 54' and the signal conductor 54" conduct electric signals to and from the first and second copolymer transducers 64' and 64" respectfully. A common ground conductor 62' serves to ground both the first and second copolymer transducers 64' and 64". The first and second copolymer transducers 64' and 64" may be used to detect an ultrasound pulse from an ultrasound scanner. The first and second copolymer transducers 64' and 64" may also be used to convert an electrical signal into an ultrasound signal for detection by an ultrasound scanner in order to aid in visualization of the medical device. The first and second copolymer transducers 64' and 64" may also be used to detect a change in the signal level of ultrasound pulses detected during the tissue manipulation process in order to determine a level of tissue manipulation.

The first and second copolymer transducers 64' and 64" may be located on opposite ends of a region of the sheath 50' which covers the freezing region of a cryosurgical medical device when installed thereon. In order to lessen the degree of thermal isolation induced by the sheath 50', the sheath can include several openings 68 which allow tissue to come in direct contact with the freezing region of the medical device.

Figure 3:
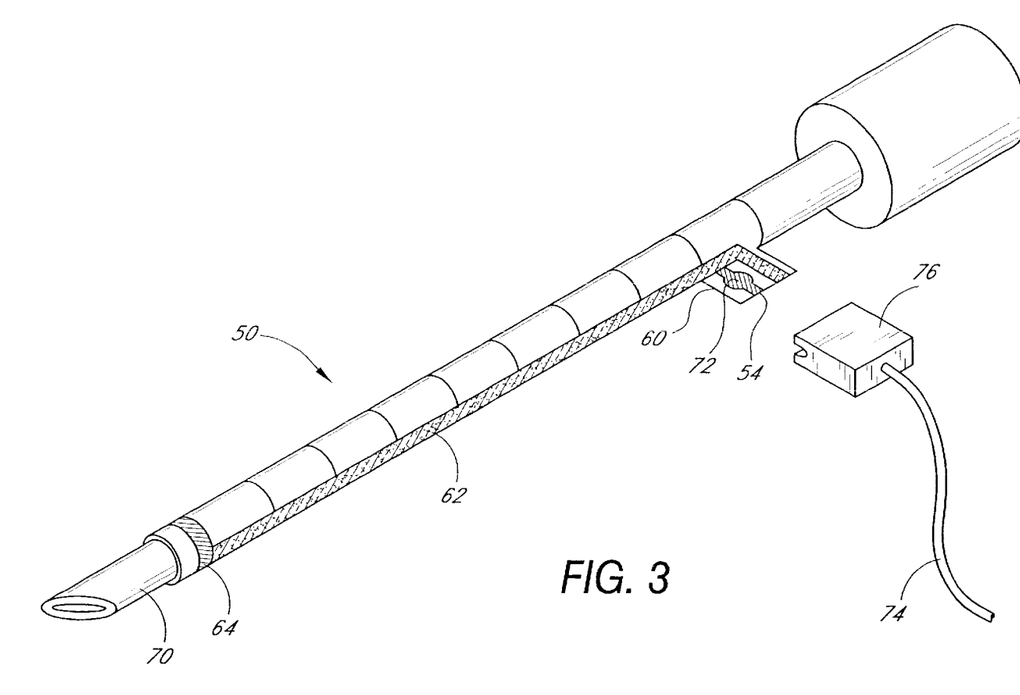
FIG. 3 is a perspective view showing a sheath installed on a medical device.

FIG. 3 is a perspective view showing the sheath 50 installed on a biopsy needle. In FIG. 3, the copolymer transducer 64 is installed in proximity to the distal end of the medical device 70. The ground conductor 62 runs down the length of the sheath 50. The signal conductor 54 is covered by the ground conductor 62 along the length of the sheath 50 except at the terminal connector 60. As noted above, the copolymer transducer 64 has a relatively high electrical impedance. The control unit connected to the sheath 50 is likely to have a much lower impedance such as on the order of 10 to 50 kΩ. In addition, the control unit is likely to be located some distance away from the medical device 70 at a comfortable viewing distance for the operator. The sheath 50 is coupled to the control unit by a length of shielded cable, twisted pair or other type of cable 74. The mismatch of impedance between the copolymer transducer 64 and the control unit make measurement of signals from the copolymer transducer by the control unit difficult or impossible. This problem is mitigated by employing a transformer in close proximity to the copolymer transducer 64.

In the embodiment of FIG. 3, a transformer 72 is attached to the signal conductor 54 and the ground conductor 62 on the terminal connector 60. The transformer 72 transforms the high impedance of the copolymer transducer 64 to a lower impedance to improve the match (and, hence, increase the power transferred) to the control unit. The transformer 72 also increases immunity to unwanted noise ingress along the length of the cable 74. In the preferred embodiment, the transformer 72 is located as close as possible to the copolymer transducer 64 in order to further reduce the susceptibility to unwanted ingress signals. However, the advantageous of proximity to the copolymer transducer 64 must be balanced against any interference with the function of the medical device 70 that might be caused thereby. For example, incorporation of a transformer adjacent to the copolymer transducer 64 may cause a bulge in the sheath and interfere with placement and removal of the device. In one embodiment, the transformer 72 is a toroid. Toroids exhibit some immunity to ingress magnetic signals as well as a broadband frequency performance. If the frequency of operation of the ultrasound source is identified, the frequency performance of the transformer may be band limited to provide rejection of unwanted signals.

In an alternative embodiment, the transformer 72 is integrated into a connector 76 which attaches the cable 74 to the terminal connector 60. In this way, the transformer 72 can be reused with another sheath 50, thus, reducing the cost of the sheath 50. In yet another embodiment, the transformer 72 is fixed to the sheath 50 or is an independent element which may be inserted into the configuration when necessary.

In one embodiment, the sheath comprises markings which facilitate placement of the medical device. For example, the sheath can be marked with centimeter markings which can be used by the operator to monitor the depth to which the device has been inserted into the patient.

Example Environments in Which the Invention may Operate

An ultrasound transducer according to the invention may be incorporated with a medical device comprising a brachytherapy needle for treating prostate cancer. Brachytherapy is a method of treating cancer by implanting seeds of radioactive material, typically iodine-125 or pallidium-103, into the cancerous tissue. The dose of radiation delivered by a seed is dependent on the nature, half-life, and quantity of seed material. Choice of the seed material and the placement locations determine the extent of the destruction of cancerous prostate tissue and, thus, are critical in the treatment of prostate cancer. A common method for calculating the total radiation delivered to the prostate is to calculate the radiation required to affect an elliptical volume of tissue. By matching this calculation to the measured volume of the prostate, a total dose of radiation delivered to a patient may be determined described in terms of the matched peripheral dose (MPD). However, the MPD does not account for position or geometry of seed placement. Thus, the success of a procedure with the correct MPD may vary significantly depending on the placement of the seeds. More recent advances employ the use of computer calculation of dose rates based on three dimensional models of the prostate generated by computerized tomography (CT), MRI, or ultrasound images. However, successful outcome of these newer methods is still dependent of the proper positioning of the seeds in the prostate. In his paper entitled "Brachytherapy in Cancer of the Prostate: An Historical Perspective" published in Volume 13 of *Seminars in Surgical Oncology*, Dr. Basil S. Hilaris states "[t]he distribution of the radioactive sources in the target volume may be critical because the radiation dose diminishes rapidly within a short distance from each source. Precise localization of radioactive sources is thus of paramount importance in brachytherapy."

The brachytherapy procedure begins by mapping the boundaries of the target tissue and the most probable locations of the cancer within the tissue. A typical method of visualizing the tissue in a minimally invasive manner is ultrasound imaging, thus, making brachytherapy a likely candidate for integration with the invention. Using prostate cancer as an example, multiple transrectal ultrasound (TRUS) images and needle biopsy samples are used to map the boundary of the prostate and the location of the lesions within the organ. The map is used to create a three dimensional grid structure as a guide for the placement of the seeds in order to achieve the desired level of destruction. This map may be generated days or weeks before the actual placement of the radiation seeds. When the map is actually used to place the seeds, it may no longer reflect the actual condition of the prostate due to biological changes such as swelling. In addition, the surgical measurements may vary compared to the mapped predictions due to changes in the calibration and positioning of equipment used in each procedure. Using the present inventions, the number of variables which can cause errors can be reduced by generating a real time image of the prostate.

Placement of the radiation seeds, such as Iodine-125 marketed by North American Scientific, North Hollywood, Calif., USA or Palladium-103 marketed by Theragenics, Norcross, Ga., USA, is typically accomplished using 16–18 gauge biopsy-like needles, such a those marketed Cook Inc., Bloomington, Ind., by placed through a stepping and stabilizing system consisting a plate with multiple holes as needle guides such as those marketed by Amertek Medical, Inc., Singer Island, Fla. or B&K Ultrasound Systems, Copenhagen, Denmark. Typically patients receiving iodine-125 require 80–100 seeds at 0.35 milliCuries (mCi) per seed up to an total absorbed dose of 140–160 gray (Gy). The present invention, when placed over a delivery needle, gives a clear indication of the location of the needle in the display of the imaging system. This image can be compared to the map of the planned seed delivery locations to aid in the placement of the seeds. In addition, the transducer may be coupled with a device that records the actual placement location of the seeds within the prostate. This record can be used to identify differences between the planned placement and the actual placement of the seeds that may affect the outcome of the procedure. In order to be adapted to operate in conjunction with a brachytherapy needle, the copolymer transducer should be placed as close as possible to the tip of the device where the seed is released. In addition, the sheath body should be constructed to avoid blocking the passageway of the needle which delivers the seed. For example, the sheath body may comprise an opening in the distal end so as not to obstruct seed delivery from the distal end of the brachytherapy needle.

In addition, the invention may be incorporated with a biopsy needle or probe used to detect breast tumors. Detection of breast cancer often begins by the palpation of suspicious lumps in the breast. These lumps can be tiny abnormalities called microcalcifications that can be the earliest or only sign of cancer. An accurate diagnosis of breast cancer can only be made by removing and performing a histological examination of the tissue. Procedures for removal of breast tissue or breast biopsy include core needle procedures and as well as more advanced procedures which use advanced probes rather than needles, such as the Mammotone Breast Biopsy System.

The core needle procedure is a nonsurgical process involving the removal of tissue through a needle. In the prior art, needle biopsy involved the stereotatic placement of a spring loaded needle within suspicious areas in the breast by using X-rays taken from two different angles. A single core sample is removed at each needle placement. A typical procedure requires 10 to 20 core samples from different placements. Thus, the procedure requires extended exposure to ionizing X-rays as well as the use of a cumbersome and expensive X-ray machine.

Placement of the needle and subsequent removal of tissue at the correct location within the breast is a critical step in the procedure. The present invention, when placed over the needle, may be used in conjunction with an ultrasound scanner, a non-ionizing imaging modality, to clearly identify the location of the needle tip. In addition, the transducer may be coupled with a device that records the actual placement of the needle, aiding in any follow up procedure which may be required. In order to be adapted to operate in conjunction with a breast biopsy needle, the copolymer transducer should be placed as close as possible to the tip the device where the tissue sample is extracted. In addition, the sheath body should be constructed to avoid blocking the passageway of the needle. For example, the sheath body may comprise an opening in the distal end so as not to obstruct tissue extraction through the distal end of the needle.

More advanced probes have been developed to execute nonsurgical procedures involving the removal of breast tissue, such as the Mammotome Breast Biopsy System developed by Biopsys Medical, Inc., Irvine Calif. The advanced probe is inserted through a tiny skin incision in the patient's breast. This suture-less, minimally-invasive incision minimizes the possibility of scarring or breast disfigurement. Tissue is drawn into the probe via a vacuum system and a high speed, rotating cutting edge advances to cut and remove the tissue. While the probe is slightly larger in diameter than the needle used in needle biopsies, the probe is able to retrieve several samples without being removed and placed in a different location in the breast. By rotating the aperture in vivo or repositioning the probe, multiple samples can be cut and collected with a single probe insertion. The samples retrieved by the probe are also larger than those retrieved by needles. In the prior art, such advanced probe procedures typically involve the stereotatic placement of probe using X-rays taken from two different angles. Thus, the procedure requires extended exposure to ionizing X-rays as well as the use of a cumbersome and expensive X-ray machine.

Placement of the probe and removal of tissue at the proper location within the breast is a critical step in the procedure. The present invention, when placed over the advanced probe, may be used in conjunction with an ultrasound scanner, a non-ionizing imaging modality, to clearly identify the location of the tissue dissection portion of the probe. In addition, the transducer may be coupled with a device that records the actual placement of the probe, aiding in any follow up procedure which may be required. In order to be adapted to operate in conjunction with an advanced probe, the copolymer transducer should be placed as close as possible to the point on the probe where the tissue samples are extracted. In addition, the sheath body should be constructed to avoid blocking the passageway of the probe. In an alternative embodiment, an ultrasound transducer may be integrated with the advanced probe rather than attached to the advanced probe by a sheath.

When used in conjunction with either a needle or a probe, placing the present invention over the needle or probe enhances the visibility of the probe on an ultrasound imaging system. The invention allows not only for the clear identification of the device within the breast, but the exact location of a specific area on the device. This ability to position the needle or probe in a location that allows the suspected tissue to be removed for examination is critical to obtaining a proper diagnosis of breast cancer.

The invention can also be incorporated into a cryosurgical probe used for ablation of carcinoma. Cryosurgery is a method for ablating tissue by removing heat energy causing tissue to freeze. The successful outcome of such a procedure depends greatly on the positioning the probe in a proper location so that the prostate tissue is destroyed but the surrounding organs and tissue is preserved. Cryosurgical probes are placed in a tissue mass using a minimally invasive visualization technique, such as ultrasound imaging. Ultrasonic visualization may be used to guide a probe into a tissue mass and to monitor the extent of tissue manipulation inflicted by the probe. As an example, cryosurgery is used to ablate the prostate as a treatment for prostate cancer. The procedure begins by visualizing the prostate with TRUS as shown below in FIG. 4. One or more cryosurgical probes is placed in the prostate through the perineum.

Although ultrasound provides a minimally invasive method to visualize the cryoprobes in the prostate, the limitations of ultrasound imaging make it difficult to precisely determine the exact location of the unaided probes in the tissue. The present invention, when placed over the cryoprobe, can be used to create an easily recognizable marker that clearly identifies the position of the cryoprobe in the prostate, even under conditions of high acoustical impedence. Information concerning enhanced positioning through the use of an ultrasound transducer which is attached to a medical device can be found in U.S. Pat. No. 5,672,172 which is assigned to the assignee of the present invention and which is incorporated in its entirety herein by this reference. Briefly, the patent describes disposing an ultrasonic transducer on a medical device. The device is exposed to an incident ultrasound signal from an ultrasound scanner. The transducer generates a corresponding electric signal and passes it to external circuitry. The external circuitry generates a responsive electric signal and couples it to the ultrasound transducer. The ultrasound transducer transduces the electrical signal into a response ultrasound signal. The responsive ultrasound signal is detected by the ultrasound scanner and creates an image in the display of the ultrasound imaging system, clearly identifying the location of the medical device. In one embodiment, the medical device comprises a manipulator for manipulating tissue within a zone of manipulation and the transducer is disposed within the zone of manipulation. The ultrasound transducer responds to receipt of an incident radiated signal by generation of a responsive radiated signal while said manipulator manipulates the issued within said zone of manipulation. In addition, the external circuitry may receive a timing signal from the scanner. The external circuitry may generate a responsive electric signal which is transduced by the transducer to create a responsive ultrasound signal even when a level of the incident ultrasound signal falls below a detectable level based upon receipt of the timing signal.

In one embodiment, a sheath comprises a copolymer transducer according to the present invention is disposed on a medical device and exposed to an incident ultrasound signal from an ultrasound scanner. The copolymer transducer generates a corresponding electric signal and passes it to external circuitry. The external circuitry generates a responsive electric signal. The ultrasound transducer transduces the electrical energy into a response ultrasound energy. The responsive ultrasound signal is detected by the ultrasound scanner and creates an image in the display of the ultrasound imaging system, clearly identifying the location of the medical device.

The ultrasound transducer can also be used to aid the process of determining the extent of tissue manipulation based upon the signal level received by the ultrasound transducer, such as is disclosed in co-pending U.S. patent application Ser. No. 08/982,753 assigned to the assignee hereof and incorporated in its entirety herein by this reference. Briefly, after insertion of the medical device within the patient, the level at which the ultrasound transducer receives the radiated signal is initially determined. As the tissue is manipulated, the signal level indication detected by the ultrasound transducer begins to change. Based upon the changes in the signal level indication and the image, the extent of tissue destruction can be determined.

In one such embodiment, the invention is installed on a cryoprobe used in cryosurgery. As noted above, cryosurgery involves the freezing of diseased tissue. Cryosurgery has been used for decades with limited success to destroy diseased tissue throughout the body. Heating or freezing tissue affects the tissue's acoustic properties. The effect is caused by changes in the transmission of ultrasound signals through the tissue as a result of the change in density of water within the tissue. Although small, the change in density of water as a function of temperature is well documented. As an example, the density of water at 38 degrees Celsius is 0.99299 gm/ml and at 70 degrees Celsius is 0.97781 gm/ml. In the case of freezing, the density of ice is 0.9170 gm/ml. These density changes affect the attenuation of the ultrasound signal transmitted between the imaging system scanner and the probe transducer during the manipulation process.

An example of the application of cryosurgery in a minimally invasive manner is the destruction of diseased prostatic tissue using small diameter cryoprobes placed through the skin into the prostate. Ultrasound imaging allows the surgeon to view the prostatic margins, bladder, urethra, and rectum. Using these organs as "landmarks," the surgeon positions the cryoprobe within the prostate to optimally destroy the diseased tissue.

After positioning the cryoprobe within the desired tissue mass, the liquid nitrogen begins to flow to the cryoprobe. Tissue begins to freeze around the tip of the cryoprobe. As the flow of liquid nitrogen continues, thermal energy is removed from an expanding area of tissue surrounding the tip of the cryoprobe. The temperature of tissue manipulated by the cryoprobe is lowest at the tip and increases outwardly to the boundary between manipulated and unaffected tissue at normal body temperature. It is generally accepted that tissue destruction occurs at temperatures below minus 60 degrees Celsius, although such factors as the speed of freezing and thawing of the tissue and the water content of the tissue affect the temperature at which tissue destruction occurs.

The ultrasound transducer placed on the cryoprobe also provides the surgeon with a method for judging the extent of the manipulation by the cryoprobe. Within the region of manipulated tissue is a boundary where tissue temperatures fall below 0 degrees Celsius. This area of frozen tissue is described as the "iceball." The boundary of the iceball is echogenic as a result of the difference in density between frozen and unfrozen tissue. As thermal energy is removed from the tissue and the iceball grows, the boundary appears as an expanding arc in the display of an ultrasound imaging system. Monitoring the growth and position of the arc gives the surgeon an indication of the extent of the manipulation of the tissue by the cryoprobe. However, as noted above, the actual destruction of tissue does not occur until the tissue reaches approximately minus 60 degrees Celsius. Therefore, the echogenic boundary is not directly indicative of the extent of tissue destruction. In addition, signals from the ultrasound imaging system are almost completely reflected at the echogenic boundary of the iceball, blocking the surgeons field of view of the tissue within the iceball.

The task of the surgeon is to destroy diseased tissue while leaving intact as much of the healthy surrounding tissue as possible. If the surgeon destroys healthy tissue, he may prolong the recovery of the patient as well as increase undesired side effects of the process. If the surgeon leaves a portion of the diseased tissue intact, the diseased tissue may continue to spread, thus, increasing the probability of subjecting the patient to a subsequent surgical procedure. Therefore, it is extremely important that the surgeon have an accurate indication of the degree of destruction of the diseased tissue. However, as noted above, the image of the iceball does not provide the surgeon with a definitive indication of the extent of tissue destruction. If the surgeon attempts to use the image of the iceball to estimate the destruction of tissue, he is likely to either destroy a significant amount of healthy tissue or to leave intact a portion of the diseased tissue.

An alternative to the above description of a manipulation process employing cryosurgery is a manipulative process involving heating of tissue. In such a case, the manipulation tool is not a cryoprobe, but rather a probe to deliver microwave, RF, or other energy form that heats tissue. Such devices are commercially available and are presently used to ablate tissue of the prostate and endometrium. Heating tissue causes cell destruction leading to necrosis of tissue within a thermal zone surrounding the heating component. Just as in cryosurgery, monitoring of the affected zone is critical during the heating process to ensure destruction of all diseased tissue and the preservation of healthy surrounding tissue.

Figure 4:
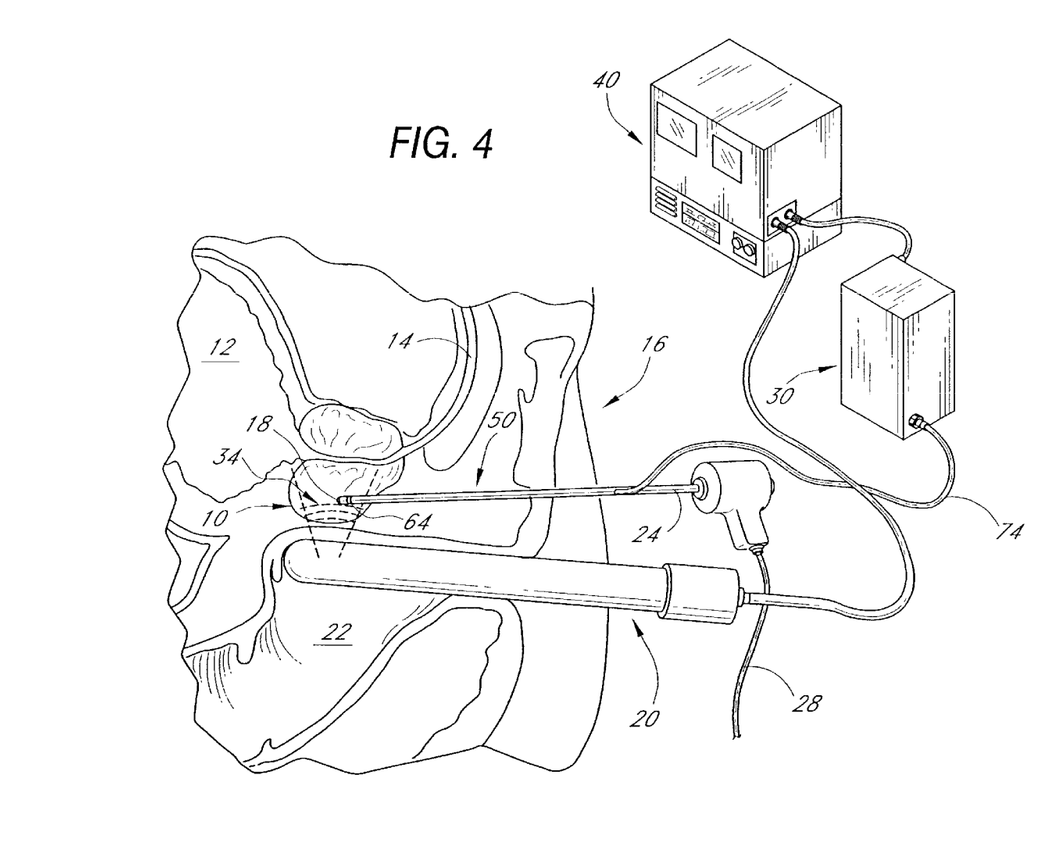
FIG. 4 is a perspective view of a configuration in accordance with the present invention portrayed as a cryosurgical probe placed within the prostate of a patient.

Referring now to FIG. 4, the present invention is shown in an exemplary application in which prostate tissue is thermally destroyed using a medical device which manipulates tissue. Before a thermal manipulation probe 16 is inserted into the body, the disposable sheath 50 is installed over a shaft 24 of the probe 16. The sheath 50 is chosen such that a snug fit to the shaft 24 is created. For example, in FIG. 4 we may assume that the sheath 50 is about 10% smaller in diameter than the shaft 24 and that it is stretched to cover the shaft 24. A snug fit between the sheath 50 and the shaft 24 serves to hold the copolymer transducer 64 firmly against the rigid shaft 24. The sheath 50 is chosen to reduce any impedance to the function of the probe 16. For example, the sheath 50 may have openings which facilitate the flow of thermal energy between the tissue and the probe 16. In addition, the sheath 50 is chosen such that the copolymer transducer 64 is located in close proximity to the area of tissue which is affected when the probe 16 is activated. In this case, the copolymer transducer 64 is collocated with the freezing chamber of the probe 16. The sheath 50 is coupled to the cable 74 to provide a connection to a signal recovery and production unit 30.

The prostate 10 is located at the neck of the bladder 12 as it forms the urethra 14. An ultrasound scanner 20 is placed in the rectum 22 and positioned such that an image of the prostate 10 may be displayed on an attached imaging system 40. The scanner 20 creates the image of the prostate 10 by transmitting ultrasound signals 34 and receiving reflections of these signals. The radiated signals 34 are reflected back to the scanner 20 from acoustic interfaces within the field of view of the scanner 20 and are used to create an image which is displayed on the imaging system 40. The copolymer transducer 64 receives the ultrasound signals 34 and creates a corresponding electric signal which is passed to the signal recovery and production unit 30. The signal recovery and production unit 30 responds by creating an electric signal that is passed to the copolymer transducer 64. The copolymer transducer 64 converts this electric signal to an ultrasound signal that is received by the scanner 20, creating a corresponding visual indication on the display of the imaging system 40. Using the image displayed on the imaging system 40, the thermal manipulation probe 16 is inserted into the body and placed such that the tip 18 of the probe 16 is located in a desired position within the prostate 10. The probe 16 may be properly placed in accordance with teachings in U.S. Pat. No. 5,672,172, incorporated herein above.

At the tip 18 of the probe 16 is a chamber into which a refrigerant fluid, typically liquid nitrogen or compressed gas, is pumped. The refrigerant is supplied to the probe 16 from a probe controller (not shown) through a refrigerant connector 28. The probe controller enables an operator to control the flow of refrigerant to the tip 18 and, hence, the freezing effect of the probe 16. When the device is activated, the refrigerant enters the chamber causing a reduction in temperature of the tip 18 of the probe 16. As the freezing process begins, a zone of frozen tissue expands outward from the tip 18.

During manipulation, the signal recovery and production unit 30 continues to receive electric signals from the copolymer transducer 64 as a result of ultrasound signals 34 received from the scanner 20. In one embodiment, the signal recovery and production unit 30 monitors the value of these electric signals over time to determine an extent of tissue manipulation. For example, the signal recovery and production unit 30 accumulates a set of values of the electric signal over time in order to determine a predicted measure of manipulation induced by the medical device. The signal recovery and production unit 30 may output a signal to the imaging system 40 so that the predicted extent of tissue manipulation may be displayed on the monitor of the imaging system 40 along with an image derived from signals generated by the scanner 20 as explained in U.S. patent application Ser. No. 08/982,753.

When the desired level of manipulation is achieved, the probe 16 is deactivated to halt the freezing process. The probe 16 is subsequently withdrawn from the patient. The sheath 50 may be disconnected from the cable 74, removed from the shaft 24 and disposed of.

A myriad of alternative embodiments will be readily apparent to one skilled in the art. For example, the ultrasound transducer may be useful for other purposes than the ones described above, such as in conjunction with laparoscopes, trocars, endoscopes, cystoscopes, or other devices designed for insertion into the body with sufficient rigidity to provide an adequate support structure.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A method of performing a medical procedure comprising ultrasound functionality comprising the steps of:

installing a disposable sheath comprising a copolymer transducer coupled to a transponder system over a medical device;

coupling said disposable sheath to a signal recovery and production unit;

exposing an area of tissue to an incident ultrasound signal from an external ultrasound imaging system;

disposing said medical device within said area of tissue; and detecting a corresponding responsive electric signal from said copolymer transducer at said signal recovery and production unit.

2. The method of claim 1, further comprising the step of responding to receipt of said corresponding electric signal by generation of a responsive electrical signal which is transduced by said copolymer transducer to create a responsive ultrasound signal.

3. The method of claim 1, further comprising the step of responding to receipt of a timing signal from a scanner by generation of said responsive electric signal which is transduced by said copolymer transducer to create said responsive ultrasound signal when a level of said incident ultrasound signal falls below a detectable level.

4. The method of claim 1, wherein said medical device is a biopsy needle.

5. The method of claim 1, wherein said medical device is a brachytherapy needle.

6. The method of claim 1, wherein said medical device is a breast biopsy probe.

7. The method of claim 1, wherein said medical device is a cryoprobe.

8. The method of claim 1, wherein said disposable sheath is intended for a single use.

9. The method of claim 1, wherein said disposable sheath comprises a sheath body constructed from polytetrafluoroethylene.

10. The method of claim 1, wherein said disposable sheath comprises a sheath body constructed from a polymer.

11. The method of claim 1, wherein said disposable sheath comprises a sheath body constructed from mylar.

12. The method of claim 1, wherein said disposable sheath comprises a stretchable sheath body constructed to be smaller tan an outside diameter of said medical device.

13. The method of claim 1, wherein said disposable sheath comprises a sheath body constructed from of a material that shrinks when exposed to some external effect.

14. The method of claim 1, wherein said disposable sheath comprises a sheath body comprises openings in order to facilitate performance of an intended purpose of said medical device.

15. The method of claim 1, wherein said signal recovery and production unit accumulates a set of values of said corresponding electric signal over time in order to determine a predicted measure of manipulation induced by said medical device.

16. The method of claim 1, wherein said disposable sheath further comprises a second piezoelectric copolymer transducer.

17. The method of claim 1, wherein said copolymer transducer is constructed from polyvinylidene difluoride (PVDF).

18. The method of claim 1, wherein said copolymer transducer is constructed from polyvinyl difluoride (PVF).

19. The method of claim 1, wherein said copolymer transducer is constructed from copolymers of vinylidene fluride.

20. The method of claim 1, further comprising the step of generating an input electric signal at said signal recovery and production unit wherein said input electric signal is transduced into an ultrasound signal radiated by said copolymer transducer.

21. The method of claim 1, further comprising the step of activating said medical device to manipulate tissue.

22. The method of claim 1, further comprising the steps of:

withdrawing said medical device from said patient;

removing said disposable sheath from said medical device; and disposing of said disposable sheath.

* * * * *